(12) United States Patent
Cuthbert et al.

(10) Patent No.: US 11,462,322 B1
(45) Date of Patent: Oct. 4, 2022

(54) METHODS OF DETERMINING A STATE OF A DEPENDENT USER

(71) Applicant: C/HCA, Inc., Nashville, TN (US)

(72) Inventors: Jeffrey Cuthbert, Littleton, CO (US); Gary Winfield, Greenwood Village, CO (US)

(73) Assignee: C/HCA, Inc., Nashville, TN (US)

( * ) Notice: Subject to any disclaimer, the term of this patent is extended or adjusted under 35 U.S.C. 154(b) by 0 days.

(21) Appl. No.: 16/700,010

(22) Filed: Dec. 2, 2019

Related U.S. Application Data

(60) Provisional application No. 62/776,786, filed on Dec. 7, 2018.

(51) Int. Cl.
*G16H 40/67* (2018.01)
*G06K 7/10* (2006.01)

(52) U.S. Cl.
CPC ......... *G16H 40/67* (2018.01); *G06K 7/10366* (2013.01)

(58) Field of Classification Search
CPC ........................... G16H 40/67; G06K 7/10366
See application file for complete search history.

(56) References Cited

U.S. PATENT DOCUMENTS

| | | | |
|---|---|---|---|
| 6,768,293 B2 | 7/2004 | Snaddon et al. | |
| 7,237,205 B2 | 6/2007 | Sarel | |
| 8,550,996 B2 | 10/2013 | Parshuram et al. | |
| 9,433,348 B2 | 9/2016 | Eshelman et al. | |
| 2003/0206116 A1 | 11/2003 | Weiner et al. | |
| 2004/0172222 A1* | 9/2004 | Simpson | G08B 21/02 702/189 |
| 2005/0113721 A1 | 5/2005 | Reed et al. | |
| 2010/0217738 A1 | 8/2010 | Sarel | |
| 2011/0291837 A1* | 12/2011 | Rantala | G16H 50/20 340/573.1 |
| 2012/0095300 A1* | 4/2012 | McNair | A61B 5/0022 600/300 |
| 2015/0141771 A1 | 5/2015 | Inbar | |
| 2016/0188832 A1 | 6/2016 | Kramer | |

* cited by examiner

*Primary Examiner* — Michael Tomaszewski
*Assistant Examiner* — Mohmad Muqueeth
(74) *Attorney, Agent, or Firm* — Kilpatrick Townsend & Stockton, LLP

(57) ABSTRACT

In some examples, a computer-implemented method for determining a state of a dependent user is provided. A flag is generated if a measured first parameter for a dependent user is within a range of values of a respective defined first parameter and a measured second parameter for the dependent user is within a range of values of a respective defined second parameter, and the measured first parameter and the measured second parameter occur within a temporal window.

15 Claims, 18 Drawing Sheets

ALERT: ROOM 5124; PT A; WBC 16.3, TEMP 95.8, ASSESS PT - RESPOND W/IN 90 MINUTES

ALERT: ROOM 6145; PT B; WBC 22.3, INR 1.6, CR 2.68, K 5.2, T$_{BILI}$ 5.17, BP 86/42; ASSESS PT- RESPOND W/IN 15 MINUTES

ALERT: ROOM 6314; PT C; LAC 3.6, RR 28, BP 83/40; SEPSIS ALERT CALLED; RESPOND W/IN 30 MINUTES

ALERT: ROOM 6303; PT D; BANDS 44, T$_{BILI}$ 2.14, TEMP 102.3, SPO2 59; AUTOMATIC RAPID CALLED

FIG. 14

METHODS OF DETERMINING A STATE OF A DEPENDENT USER

CROSS-REFERENCE TO RELATED APPLICATIONS

This application claims priority under 35 U.S.C. § 119 to U.S. Provisional Application No. 62/776,786, filed Dec. 7, 2018, which is hereby incorporated by reference in its entirety for all purposes.

BACKGROUND

This specification relates in general to determining a state of a dependent user. Such an determination may be critical in identifying a protocol to address the state of the dependent user. However, existing methods of determining the state of the dependent user may be slow, burdensome, and inaccurate.

SUMMARY

Exemplary embodiments of the invention provide systems and methods for determining a state of a dependent user. According to an aspect of the invention, a computer-implemented method of determining a state of a dependent user includes receiving data for the dependent user. The data includes a plurality of measured first parameters and a plurality of measured second parameters. The computer-implemented method also includes accessing a rule set for the dependent user. The rule set includes a range of values for each of a plurality of defined first parameters and a range of values for each of a plurality of defined second parameters. For a subset of the data that is collected within a temporal window, and for at least one measured first parameter of the plurality of measured first parameters, the computer-implemented method includes comparing the measured first parameter with a respective one of the plurality of the defined first parameters to determine whether the measured first parameter is within the range of values for the respective one of the plurality of defined first parameters. For the subset of the data that is collected within a temporal window, and for at least one measured second parameter of the plurality of measured second parameters, the computer-implemented method includes comparing the measured second parameter with a respective one of the plurality of the defined second parameters to determine whether the measured second parameters is within the range of values for the respective one of the plurality of defined second parameters. If it is determined that at least one of the measured first parameters is within the range of values for the respective one of the plurality of the defined first parameters and it is determined that at least one of the measured second parameters is within the range of values for the respective one of the plurality of the defined second parameters, the computer-implemented method also includes generating a flag, and outputting a message including an identifier of the dependent user, the flag, the at least one of the measured first parameters that is within the range of values for the respective one of the plurality of the defined first parameters, and the at least one of the measured second parameters is within the range of values for the respective one of the plurality of the defined second parameters.

The computer-implemented method may also include processing the data to filter out invalid entries. The rule set may be a function of a classification of the dependent user. Alternatively or in addition, the rule set may be a function of a location of the dependent user.

The message may also include a level of response for the state of the dependent user. Further, the message may also include a time frame for the response. The flag may indicate the state of the dependent user.

Other objects, advantages, and novel features of the present invention will become apparent from the following detailed description of the invention when considered in conjunction with the accompanying drawings.

BRIEF DESCRIPTION OF THE DRAWINGS

Various examples in accordance with the present disclosure will be described with reference to the drawings, in which:

FIG. 12 is an example of a dashboard that may be generated by the techniques described herein;

FIG. 14 shows examples of detailed alerts that may be generated by the techniques described herein;

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Figure 1:
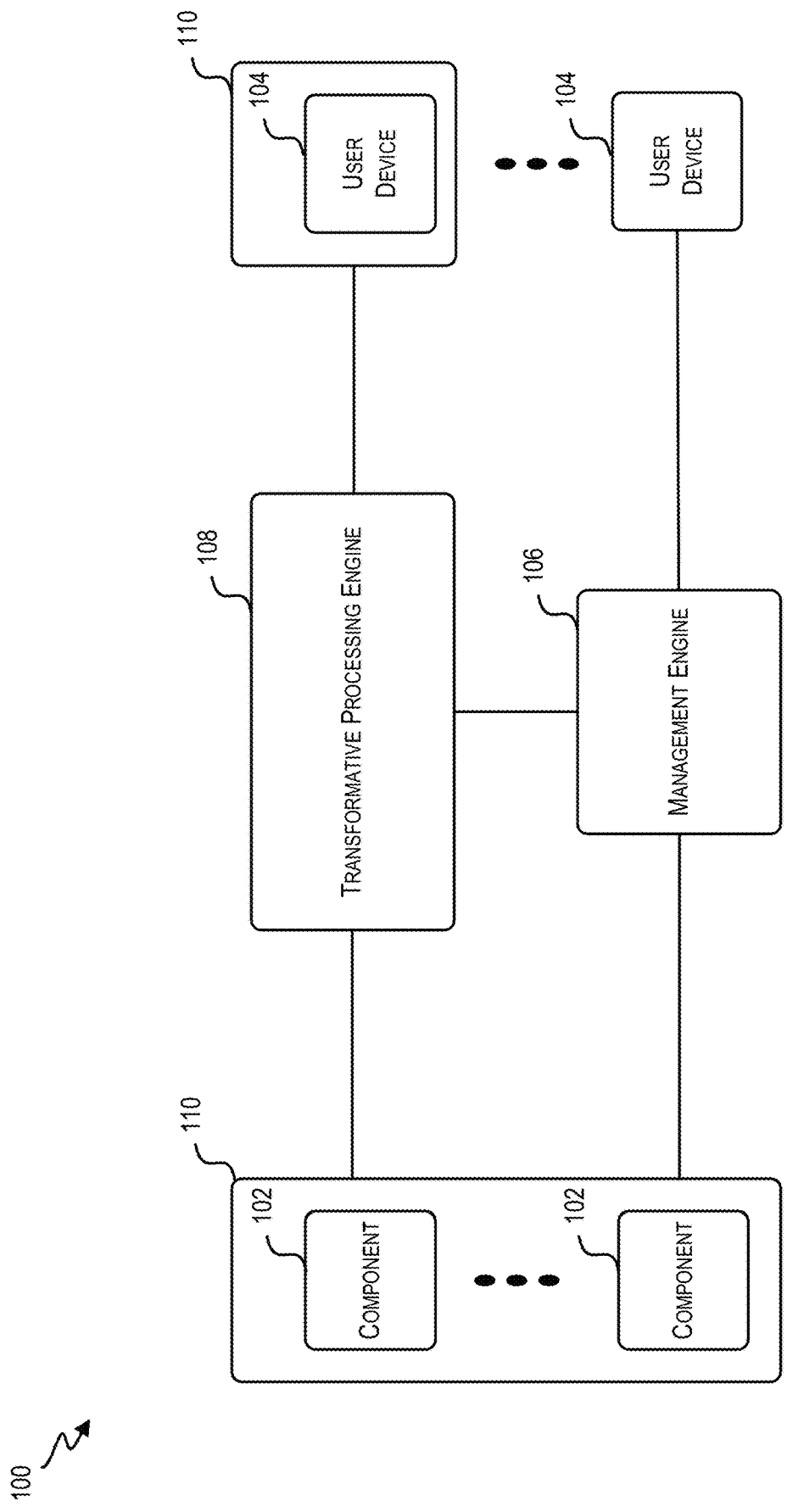
FIG. 1 is an example block diagram illustrating an interaction system in which techniques relating to determining a state of a dependent user may be implemented, according to at least one example.

Referring first to FIG. 1, a block diagram of an example of an interaction system 100 is illustrated. Generally, in interaction system 100, data can be generated at one or more system components 102 and/or user devices 104. Management engine 106 can manage the flow of communications within interaction system. Transformative processing engine 108 can receive, intercept, track, integrate, process, and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102, and/or data in a corresponding communication received from a user device.

As another example, a user device 104 can be configured to detect input received at an interface of the device. The input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect input requesting particular data, to generate a request communication (e.g., to be sent to transformative processing engine), to receive the requested data and/or to present the received data.

The depicted engines, devices and/or components can communicate over one or more networks. A network of one or more networks can include a wired network (e.g., fiber, Ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or focus. Exemplary types of facilities include server farm facilities, web-server facilities, data-storage facilities, telecommunication facilities, service facilities, and/or operational facilities. For example, a first facility may include a structure at a first location at which one or more resources (e.g., computational resources, equipment resources, laboratory resources, and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another example, different facilities may include resources of similar or same types but may vary in terms of, for example, accessibility, location, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing, and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client, or receiving a service from the client.

In some examples, one or more components 102 and one or more user devices 104 may communicate with transformative processing engine 108 and management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., management engine 106, an entity device, and/or a user device) and/or locally or remotely stored. In some examples, transformative processing engine 108 receives data in a particular format (e.g., the HL7 format) or conforming to any other suitable format and/or is configured to transform received data to conform to the particular format.

One or more components 102 of facility 110 can include and/or has access to a local or remote memory for storing generated data. In some examples, the data is stored by one or more servers local to facility 110. The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from a component (or facility), the record service can identify a corresponding record and update the record to include the data (or processed version thereof). In some examples, the record service provides data to transformative processing engine 108.

Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private, and/or proprietary network or protocols. The use of one or more private and/or proprietary protocols can promote secure transfer of data.

Figure 2:
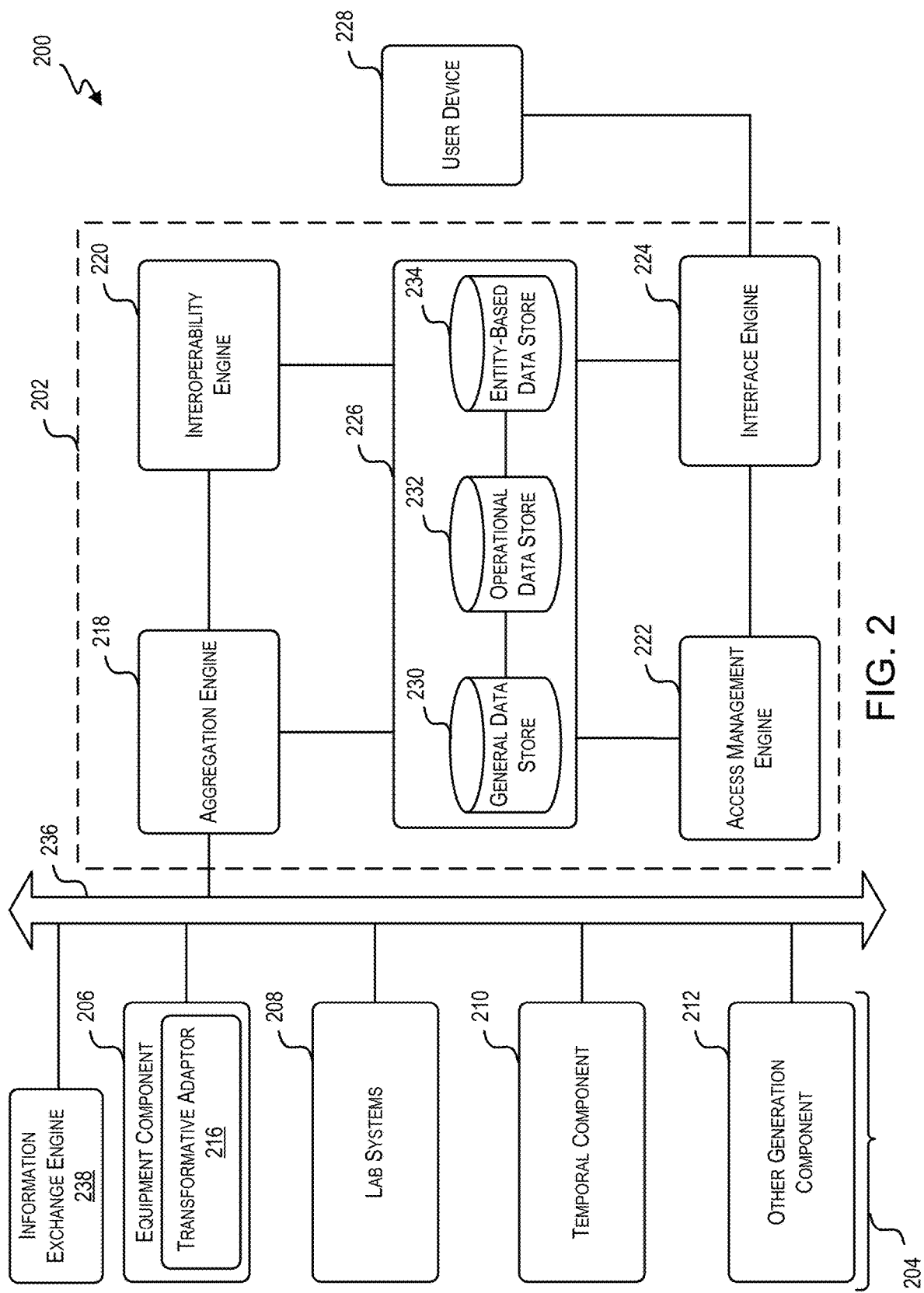
FIG. 2 is an example block diagram illustrating an interaction system in which techniques relating to determining a state of a dependent user may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 include an equipment component 206, a lab systems component 208, a temporal component 210, and other generation component 212. One or more generation components 204 are examples of one or more components 102 discussed with reference to FIG. 1. In some examples, the data may pass to the transformative processing engine 202 via an information exchange service bus 236 (e.g., an enterprise service bus). In some examples, only a portion of the is passed via the information exchange service bus 236, while other portions are passed directly to the transformative processing engine 202 without first passing over the information exchange service bus 236.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design—making large amounts of data, in many different originating formats available to various types of users, via one or more interfaces. At least a portion of the data generated by the generation components 204 may be provided to the transformative processing engine 202. In some examples, each generation component 204 includes an agent that executes on the generation components 204 and determines which data to send to the transformative processing engine 202 and other engines described herein. In some examples, the generation components 204 provide data to the transformative processing engine 202 via a messaging bus (e.g., an information exchange service bus 236). The messaging bus, which may be included in the transformative processing engine 202 or separate, is able to see data that moves throughout the interaction system 200. The information exchange service bus 236 also includes a subscription registry that can be used to manage subscriptions to the information exchange service bus 236 for certain data (e.g., data having certain characteristics). The information exchange service bus 236 may send and/or direct data to certain other entities when appropriate as indicated by subscription records in the registry.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Temporal component 210 may include any suitable computing devices used with respect to interaction system 200. For example, temporal component 210 can be configured to allocate a resource to a particular entity during a particular temporal window. Temporal component 210 can monitor a schedule for the resource and can identify one or more available temporal windows that may be secured by a particular entity. Upon receiving an indication, temporal component 210 may update a schedule of a resource to reflect that a particular temporal window is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the location and other details about the component or the user device. In some examples, the component and the user device may include global positioning chips that are configured to determine a geolocation.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine, and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, and the like. Access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

As described herein, an information exchange engine 238 shares a network connection with the information exchange service bus 236. The information exchange engine 238 is configured to monitor data (e.g., messages) that is passed over the information exchange service bus 236 and, from the monitored data, select certain portions to provide to one or more authorized user devices. The information exchange engine 238 is also configured to route inbound messages and route outbound messages, as described herein. The information exchange engine 238 is also configured to generate customized messages based on dependent user data.

Figure 3:
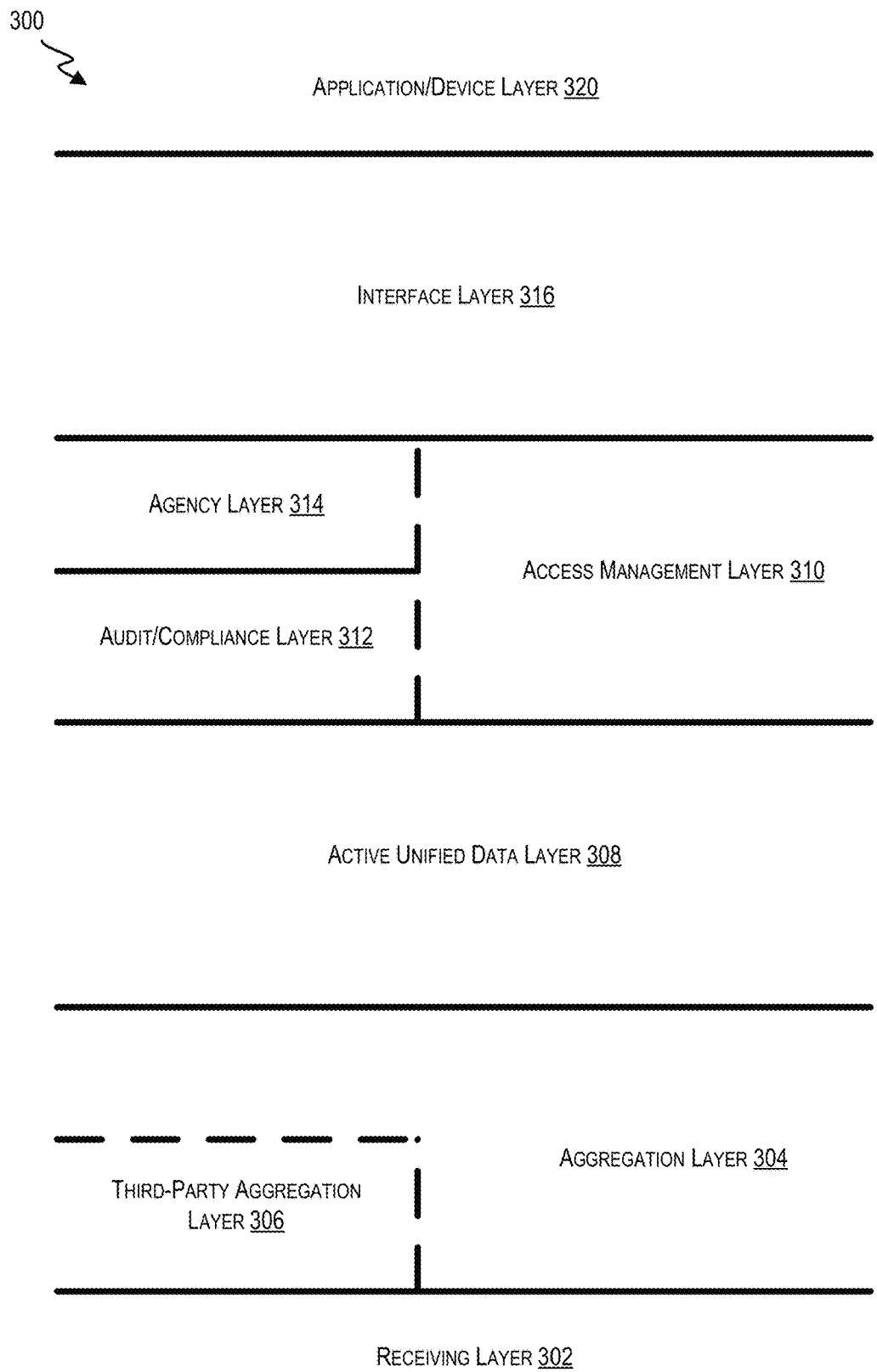
FIG. 3 is an example schematic model illustrating a network communication model in which techniques relating to determining a state of a dependent user may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum, or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties.

Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
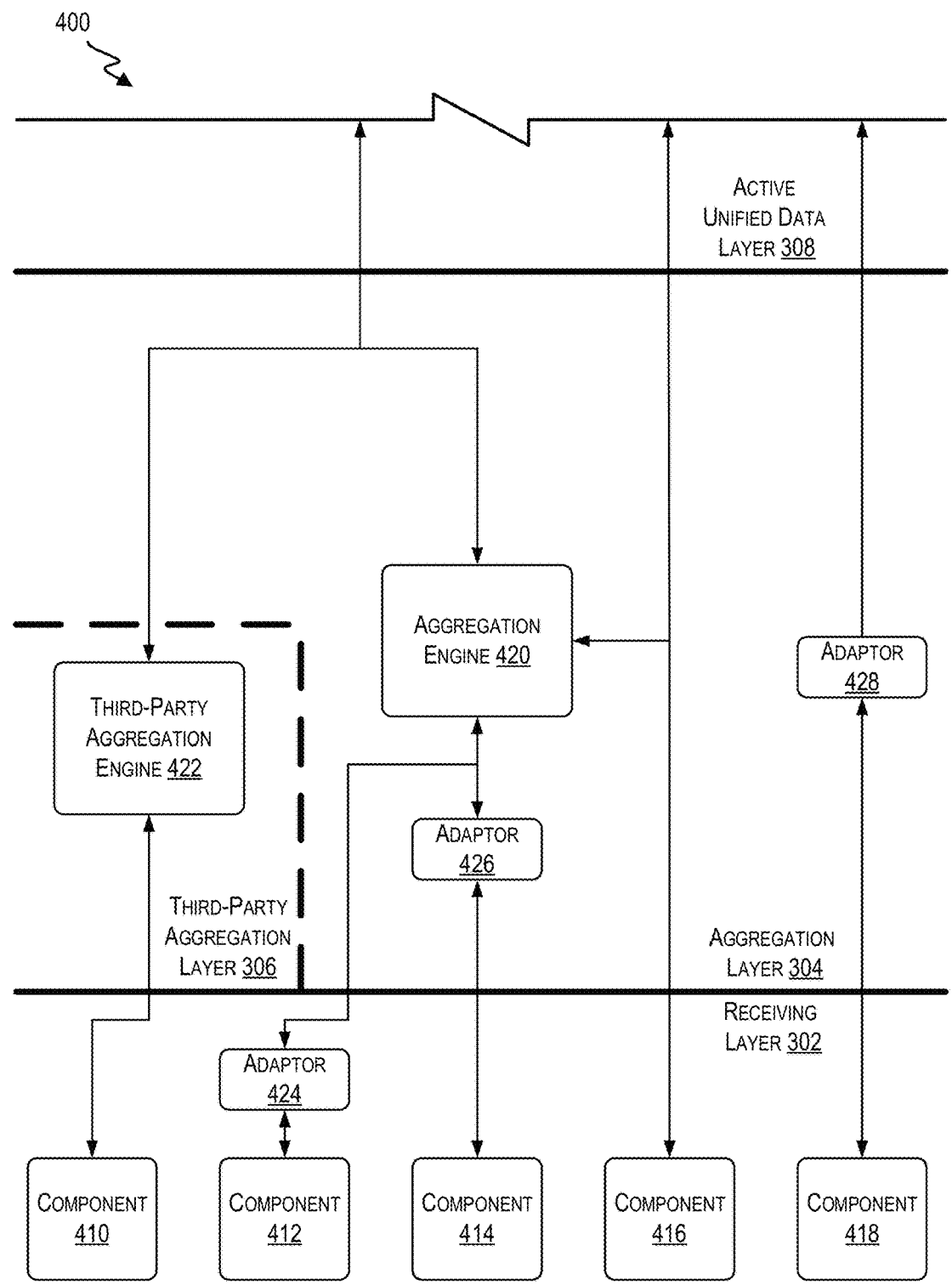
FIG. 4 is an example schematic model illustrating an aspect of the network communication model of FIG. 3 in more detail.

Turning next to FIG. 4, a diagram 400 is shown that depicts a portion of architecture stack 300 according to at least one example. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

The diagram 400 also includes the information exchange service bus 236 and the information exchange engine 238. As introduced herein, messages passing through the aggregation layer 304 can pass over the information exchange service bus 236. In this manner, the information exchange engine 238 can access the messages, route the messages, and/or customize the messages.

Figure 5:
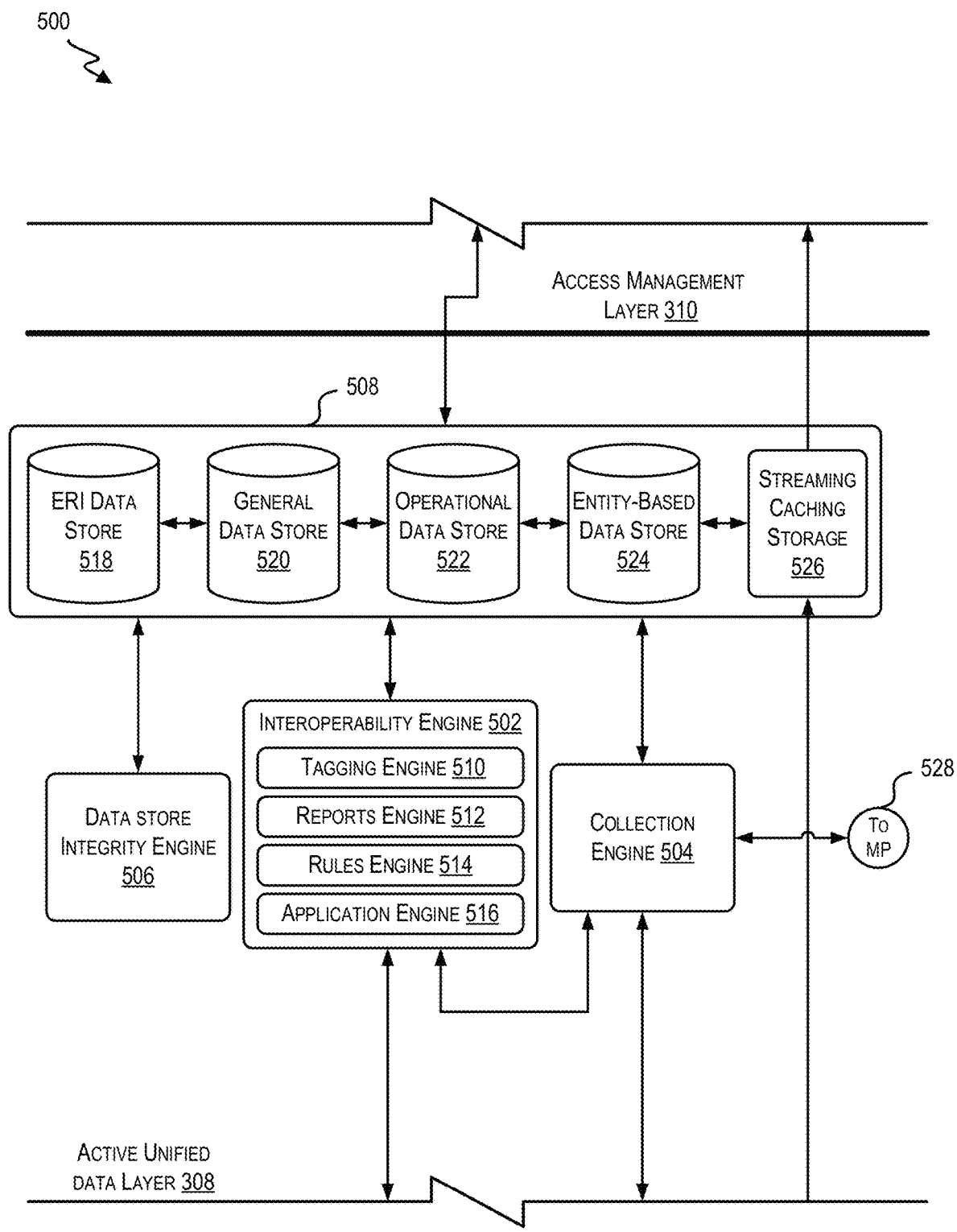
FIG. 5 is an example schematic model illustrating an aspect of the network communication model of FIG. 3 in more detail.

Referring next to FIG. 5, a diagram 500 is shown that depicts a portion of architecture stack 300 according to at least one example. In particular, diagram 500 includes active unified data layer 308 and a portion of access management layer 310. Active unified data layer 308, as illustrated in diagram 500, includes an interoperability engine 502 (e.g., interoperability engine 220), a collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304.

In some examples, the table also includes information for tracking the progress of the message from an origination node to a destination node. For example, typically when a message (e.g., any communication of data) is first received by transformative processing engine 108 (e.g., interoperability engine 502), management engine 106 (e.g., collection engine 504 of management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to management engine 106 that it saw the message. In this manner, management engine 106 may track messages from end-to-end for the life of the message.

In one example, the messages are requests. The requests may be generated based om user input at one of the components. The requests may be received by transformative processing engine 108 and integrated into the system. In some examples, management engine 106 may be notified that the requests have been received and may therefore be configured to generate message IDs for each request. These message IDs may then be associated with each of the requests. As the requests continue to move throughout the interaction system (e.g., away from transformative processing engine 108), management engine 106 may track their movement using the message IDs. If one of the requests does not arrive at its destination, management engine 106 may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, management engine 106 (e.g., collection engine 504 of management engine 106) may receive the message and/or message identifier directly from one of components 410-418. For example, one of components 410-416 may be configured to generate the unique message identifier and/or communicate directly with management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, collection engine 504 provides unique message identifiers to other elements of the interaction system to monitor the messages as they move throughout the interaction system. Collection engine 504 also provides a portion of the unique message identifiers to a management platform (indicated by a circle 528) for further analysis of the message identifiers. Such analyses may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("ERI data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within ERI record data store 518 is retained data. In some examples, the information within ERI record data store 518 is organized according to entity identifying information. Thus, ERI record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. In some examples, the operational data store 522 includes data pertaining to decision making as discussed herein and other data typically used.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
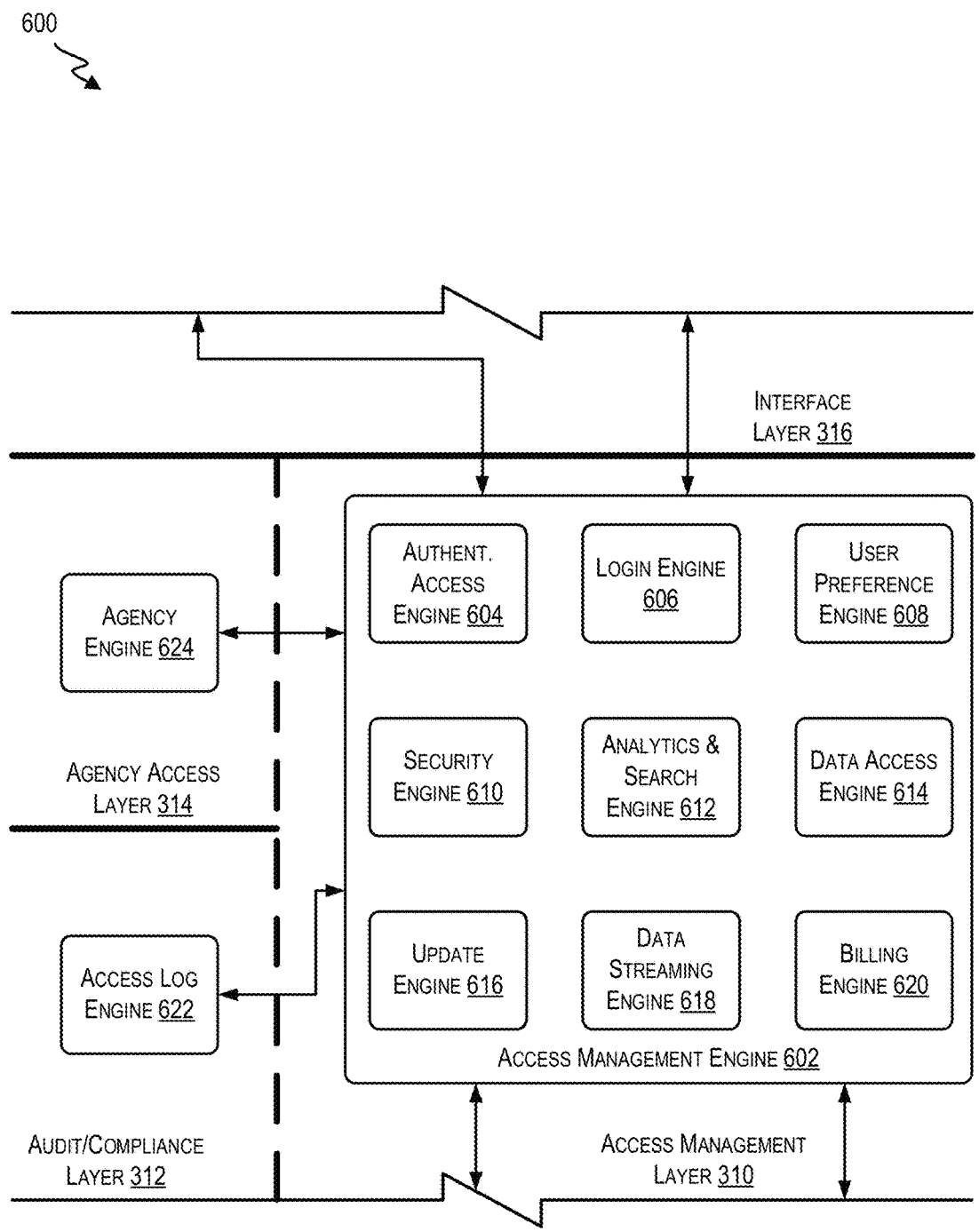
FIG. 6 is an example schematic model illustrating an aspect of the network communication model of FIG. 3 in more detail.

FIG. 6 shows a diagram 600 which depicts a portion of architecture stack 300 according to at least one example. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions, and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. In some examples, agency engine 624 may be used to track one or more performance indicators identified by a government agency and/or to provide report instances of defined types of events. In some examples, a university is an agency that uses agency engine 624 to collect data pertaining to one or more studies. Agency engine 624 can collect the pertinent data, potentially format and/or analyze the data, and facilitate transmission of the data to the appropriate agency.

Figure 7:
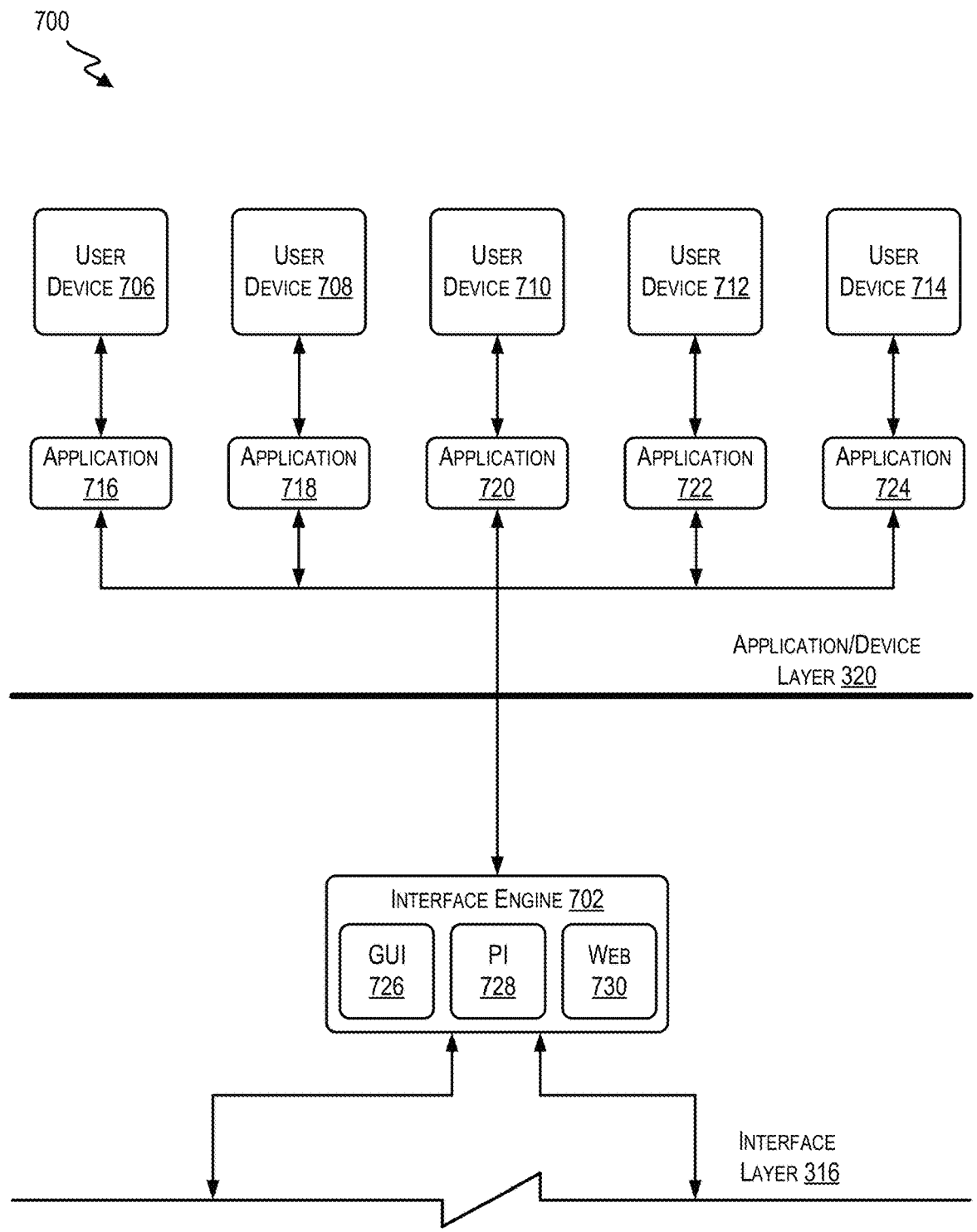
FIG. 7 is an example schematic model illustrating an aspect of the network communication model of FIG. 3 in more detail.

FIG. 7 shows a diagram 700 which depicts a portion of architecture stack 300 according to at least one example. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system.

For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 706-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for a particular entity. In some examples, application 720 may present different data depending on a focus of the entity and protected information associated with the entity. In this manner, application 720 adapts and automatically adjusts depending on the context in which the entity is using the application. Application 720 may be configured to receive input, adjust presentations, present unprompted alerts, adjust display of content, move more relevant content to the foreground, move less relevant content to the background, and/or populate forms for the entity.

In another example, application 722 may be specific for nurses or types of nurses. In this example, application 722 may include dashboards, widgets, windows, icons, and the like that are customized to individual nurses. Similar to the example discussed above pertaining to the user, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data. In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
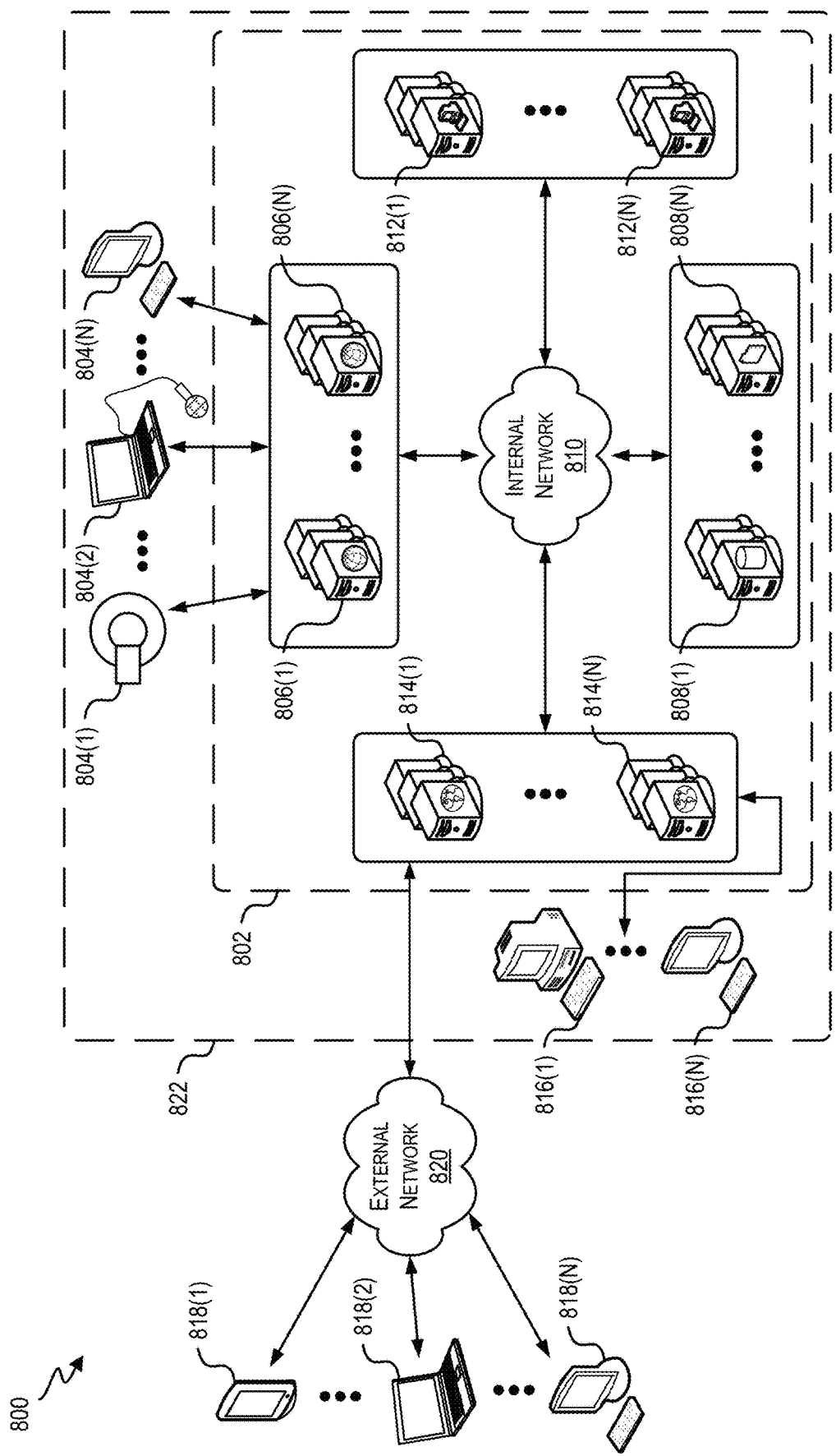
FIG. 8 is an example schematic architecture illustrating an interaction system in which techniques relating to determining a state of a dependent user may be implemented, according to at least one example.

Turning now to FIG. 8, an interaction system 800 is shown according to at least one example. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806(1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

The systems, environments, devices, components, models, and the like of FIGS. 1-8 may be used to implement a particular system as described herein with reference to later figures. In one example, a computer-based method predicts a state of a dependent user based on unique combinations of first parameter data and second parameter data. The first parameter data and the second parameter data are received from a data warehouse periodically and processed. For example, 12 first parameters and 6 second parameters may be considered, totaling 278,460 potential unique combinations. Each rule set may include a defined high value and/or a defined low value for a plurality of first parameters, a defined high value and/or a defined low value for a plurality of second parameters, and an indication of a dependent user type. To trigger a flag based on a rule set, both a measured first parameter and a measured second parameter must be within their respective defined ranges (e.g., high or low) within a temporal window such as 36 hours. For example, the temporal window may be measured retrospectively from the current time. The ranges indicate values that are considered to put the dependent user at risk for deterioration. As more flags are triggered, it becomes more likely that the state of the dependent user is deteriorating. A notification about the triggered flags may be output. A dependent user may begin triggering flags on average 24 hours before an event occurs that causes rapid deterioration, such that the flags serve as an early warning sign and provide an opportunity for early intervention.

The rule set may be selected as a function of the type of dependent user. Multiple rule sets may be tuned for multiple types of dependent users. Multiple rule sets may also be tuned for multiple sub-types of dependent users. Alternatively or in addition, multiple rule sets may also be tuned for different geographic regions and/or dependent user populations. Alternatively or in addition, multiple rule sets may also be tuned for a specific location. In some examples, the rule sets may be tuned by analyzing retrospective data and adjusting the defined high values and/or the defined low values of the plurality of first parameters and/or the plurality of second parameters to maximize the sensitivity.

In another example, a computer-based method uses the flags representing unique combinations of first parameter data and second parameter data to determine a relevance. For example, the method may know that if flags 1 and 10 are triggered, the dependent user is deteriorating and the deterioration likely has a first cause. However, if flags 1 and 12 are triggered, the deterioration likely has a second cause that is different from the first cause. Once a state of the dependent user has been determined, a set of suggestions can be presented to address the state of the dependent user. The methods discussed herein may be implemented using virtual computing resources and/or in a web-based environment.

Figure 9:
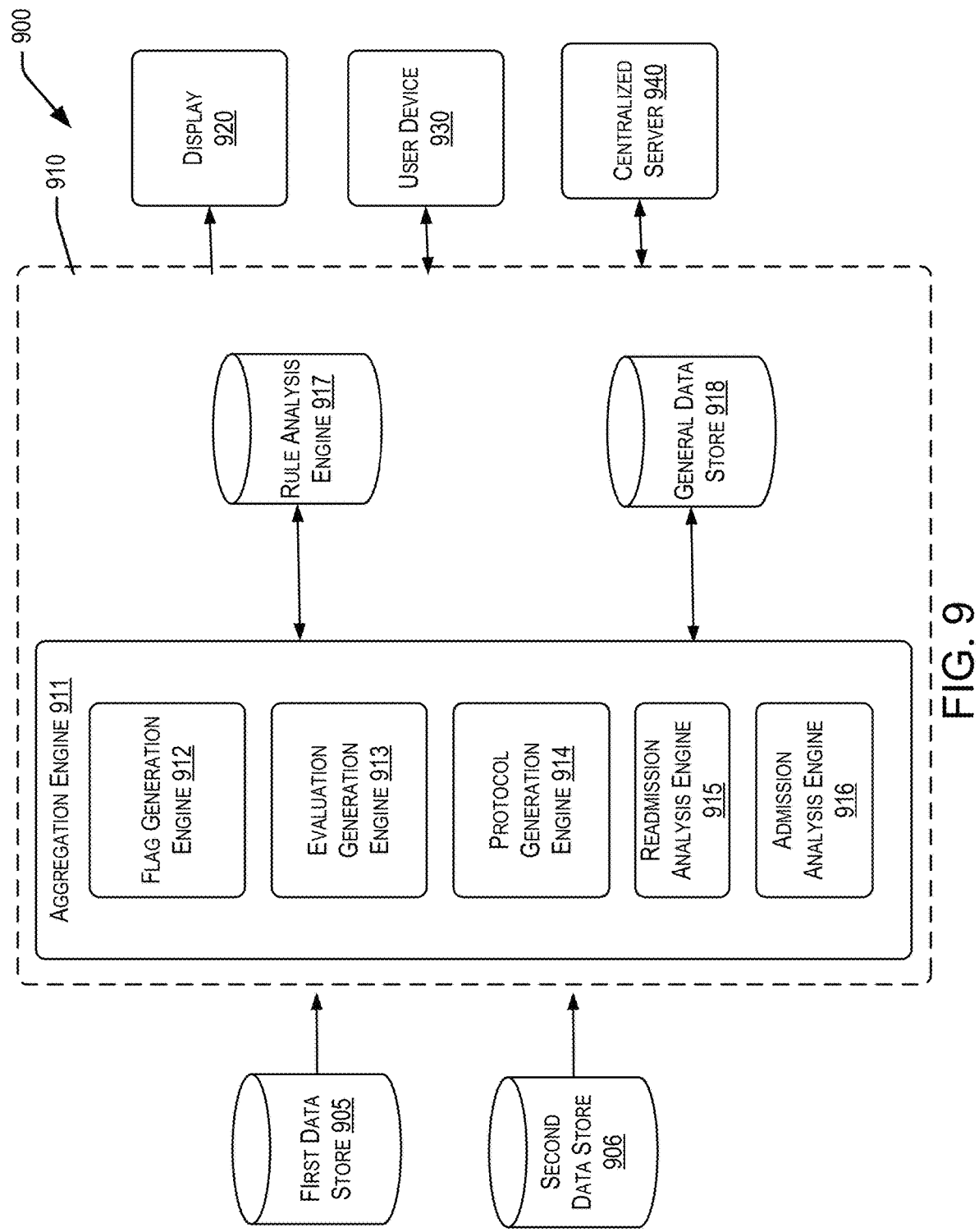
FIG. 9 is an example block diagram of an example of a network in which techniques relating to determining a state of a dependent user may be implemented, according to at least one example.

Referring now to FIG. 9, a block diagram of an example of a network 900 is shown. The network 900 includes a transformative integration engine 910. The transformative integration engine 910 is an example of the transformative integration engine 108 discussed with reference to FIG. 1. The transformative integration engine 910 includes an aggregation engine 911, a rule analysis engine 917, and a general data store 918. The aggregation engine 911 is an example of the aggregation engine 218 discussed with reference to FIG. 2.

Generally the aggregation engine 911 is configured to collect data from various sources and to perform one or more operations on the collected data. For example, the aggregation engine 911 may collect first data from a first data store 905 and second data from a second data store 906. The first data store 905 and the second data store 906 may be housed and/or accessed via a virtual application. The first data store 905 may include a Cloudera data stack having raw HL7 data feeds from electronic records. The aggregation engine 911 may be associated with a particular facility within the network 900, with a plurality of facilities within the network 900, or with the entire network 900. Although only a single aggregation engine 911 is shown, a plurality of aggregation engines may be provided, and each aggregation engine may be associated with a different facility within the provider network 900.

The first data may include measured first parameters and measured second parameters for a plurality of dependent users at a facility within the network 900. The first data may also include demographic information about each dependent user. In addition, the first data may include a classification of each dependent user. The first data may also include the date and time that each measured first parameter and each measured second parameter was measured. The first data may be filtered to remove any invalid and/or impossible results.

The second data may include a plurality of rule sets. Each rule set may include ranges of values for defined first parameters and defined second parameters. Each of the ranges may be selected such that a measured value within the range may indicate that a state of a dependent user is deteriorating, and/or that the dependent user will likely be transferred.

The first data and the second data may be updated periodically, such as every minute, every thirty minutes, every hour, every two hours, every four hours, every day, every week, or every month. Further, the first data and the second data may be sent to the transformative integration engine 910 periodically, such as every minute, every thirty minutes, every hour, every two hours, every four hours, every day, every week, or every month. The aggregation engine 911 may aggregate the data periodically at any suitable interval.

The rule analysis engine 917 may determine which of the rule sets applies in a particular situation. For example, the rule analysis engine 917 may select a rule set based on the location of the facility and/or the dependent user. For example, the ranges of the values within the rule set may be different based on the altitude of the facility or the dependent user population of the facility. Alternatively or in addition, the rule analysis engine 917 may select a rule set based on the classification of the dependent user.

The aggregation engine 911 may aggregate some or all of the data by layering the rule set on the first data. The aggregation engine 911 may include various engines for aggregating the data, such as a flag generation engine 912, an evaluation generation engine 913, a protocol generation engine 914, a readmission analysis engine 915, and an admission analysis engine 916. These engines will be described in further detail below. After aggregating the data, the aggregation engine 911 may send the results to a general data store 918, which is configured to store the results. Further, the transformative integration engine 910 may output the results to a display 920, a user device 930, and/or a centralized server 940.

FIGS. 10, 13, 16, 17, and 18 illustrate example flow diagrams showing processes 1000, 1300, 1600, 1700, and 1800, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

Figure 10:
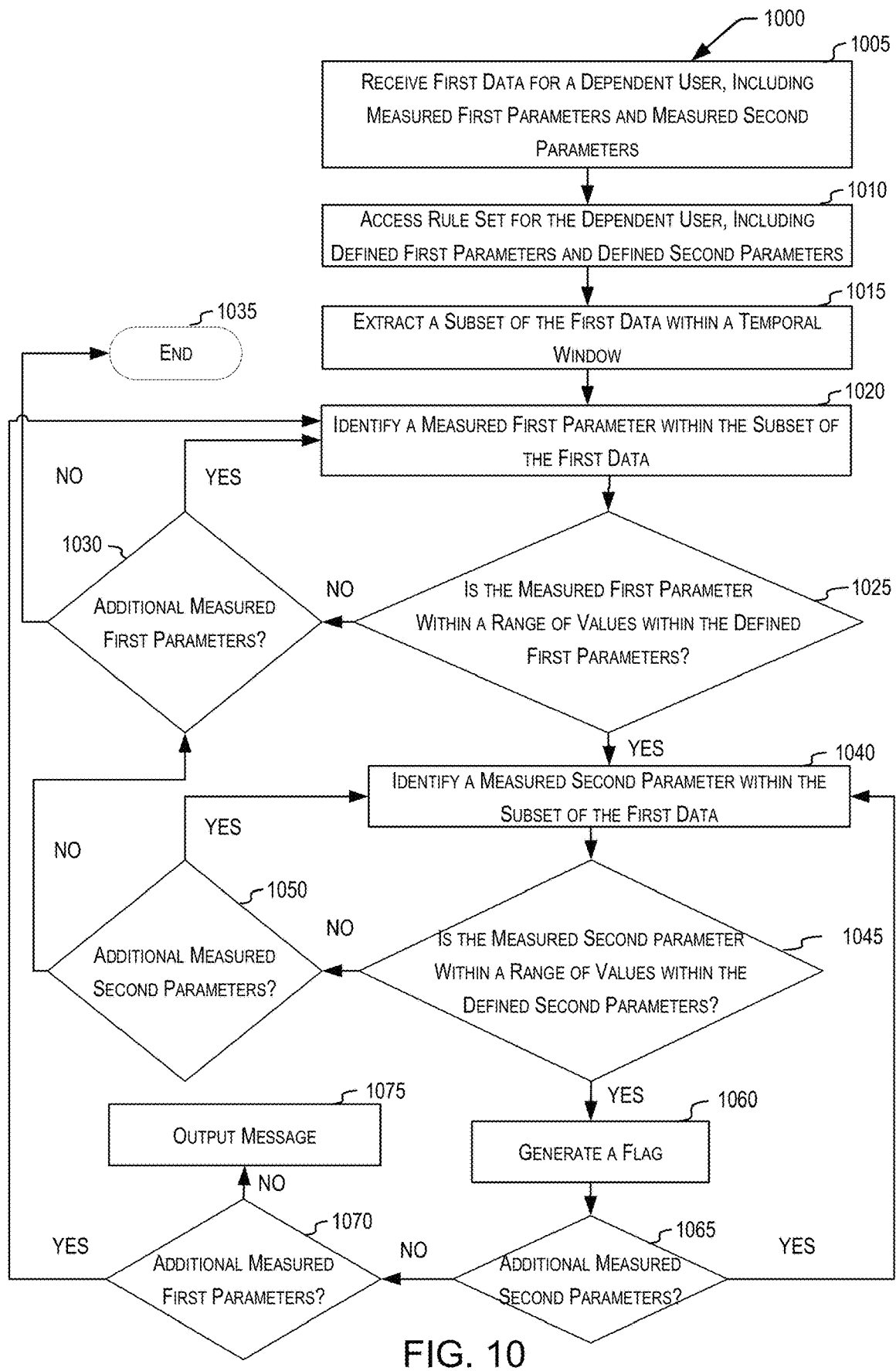
FIG. 10 is an example flowchart of a method in which techniques relating to determining a state of a dependent user may be implemented, according to at least one example.

Referring now to FIG. 10, a flowchart of a method 1000 according to an example is shown. The method 1000 may generate at least one flag that indicate the state of the dependent user. The method 1000 may be performed by the flag generation engine 912 shown in FIG. 9.

The method 1000 begins at block 1005 where first data is received for a dependent user. The first data may be received from first data store 905. The first data includes measured first parameters and measured second parameters for the dependent user. Further, the first data may include a classification of the dependent user. The first data may also include the date and time that each measured first parameter and each measured second parameter was measured.

A rule set for the dependent user is accessed at block 1010. The rule analysis engine 917 may identify the rule set based on the classification of the dependent user and/or the geographic location where the facility is located. The rule set may be accessed from rule set data store 906. The rule set may include ranges of values for defined first parameters and defined second parameters for the dependent user.

The method 1000 then extracts a subset of the first data for the dependent user that falls within a temporal window at block 1015. The subset of the first data includes measured first parameters and measured second parameters for the dependent user. The temporal window may have any suitable duration, such as 12 hours, 24 hours, 36 hours, or 48 hours. The duration of the temporal window may be determined by the classification of the dependent user.

A measured first parameter within the subset of the first data is identified at block 1020. It is determined whether the measured first parameter is within the range of values for the corresponding defined first parameter at block 1025. The range of values may indicate that the dependent user is more likely to deteriorate. For example, a dependent user having a white blood cell count of 14,000 per microliter would be within the range of values for the white blood cell count of less than 3,000 per microliter or greater than 12,000 per microliter.

If it is determined that the measured first parameter is not within the range of values for the corresponding defined first parameter at block 1025, then method 1000 determines if there are any additional measured first parameters within the subset of the first data at block 1030. If there are no additional measured first parameters, method 1000 ends at block 1035. In this example, no flags would be generated for the dependent user. On the other hand, if there are additional measured first parameters, method 1000 returns to block 1020 to identify and analyze another one of the measured first parameters.

If it is determined that the measured first parameter is within the range of values for the corresponding defined first parameter at block 1025, then method 1000 identifies a measured second parameter within the subset of the first data at block 1040. It is determined whether the measured second parameter is within the range of values for the corresponding defined second parameter at block 1045. The range of values may indicate that the dependent user is more likely to deteriorate. For example, a dependent user having a systolic blood pressure of 80 mm Hg would be within the range of values for the systolic blood pressure of less than 90 mm Hg.

If it is determined that the measured second parameter is not within the range of values for the corresponding defined second parameter at block 1045, then method 1000 determines if there are any additional measured second parameters within the subset of the first data at block 1050. If there are no additional measured second parameters, method 1000 returns to block 1030, where it is determined if there are any additional measured first parameters. On the other hand, if there are additional measured second parameters, method 1000 returns to block 1040 to identify and analyze another one of the measured second parameters.

If it is determined that the measured second parameter is within the range of values for the corresponding defined second parameter at block 1060, then method 1000 generates a flag at block 1060. The flag includes the measured first parameter that is within the range of values of the defined first parameters, as well as the measured second parameter that is within the range of values of the defined second parameters. Each flag is a unique combination of a measured first parameter and a measured second parameter. For example, if there are 12 defined first parameters and 6 defined second parameters, a total of 72 flags may be generated as unique combinations of a measured first parameter and a measured second parameter.

It is determined if there are any additional measured second parameters within the subset of the first data at block 1065. If there are additional measured second parameters, method 1000 returns to block 1040 to identify and analyze another one of the measured second parameters. On the other hand, if there are no additional measured second parameters, it is determined if there are any additional measured first parameters within the subset of the first data at block 1070. If there are additional measured first parameters, method 1000 returns to block 1020 to identify and analyze another one of the measured first parameters. If there are no additional measured first parameters, method 1000 ends at block 1075 by outputting a message. The message may include all of the flags that were generated, and each flag includes a unique combination of a measured first parameter and a measured second parameter. Each flag may include an identifier, a value, and a measurement time of the measured first parameter, as well as an identifier, a value, and a measurement time of the measured second parameter. The message may also include additional information about the dependent user. The message may be output to display 920, user device 930, and/or centralized server 940. Alternatively or in addition, the message may be stored in general data store 918.

Figure 11:
FIG. 11 is an example of a rule set that may be used by the techniques described herein.

FIG. 11 shows an example of a rule set 1100 according to an embodiment of the invention. Rule set 1100 includes ranges of values 1110 for defined first parameters 1105 and ranges of values 1120 for defined second parameters 1115. Ranges of values 1110 and/or 1120 are merely exemplary, and may be adjusted as appropriate. Ranges of values 1110 and/or 1120 may include ranges that indicate that the state of a dependent user is deteriorating. Further, ranges of values 1110 and/or 1120 may include cutoffs to ensure that the ranges only include valid values. This filters out any invalid results. This may prevent measured data that was input incorrectly from erroneously generating a flag.

As discussed above, the ranges of values 1110 and/or 1120 within rule set 1100 may be different based on the location of the dependent user. Further, the ranges of values 1110 and/or 1120 within rule set 1100 may be different based on the classification or a sub-classification of the dependent user.

Figure 12:
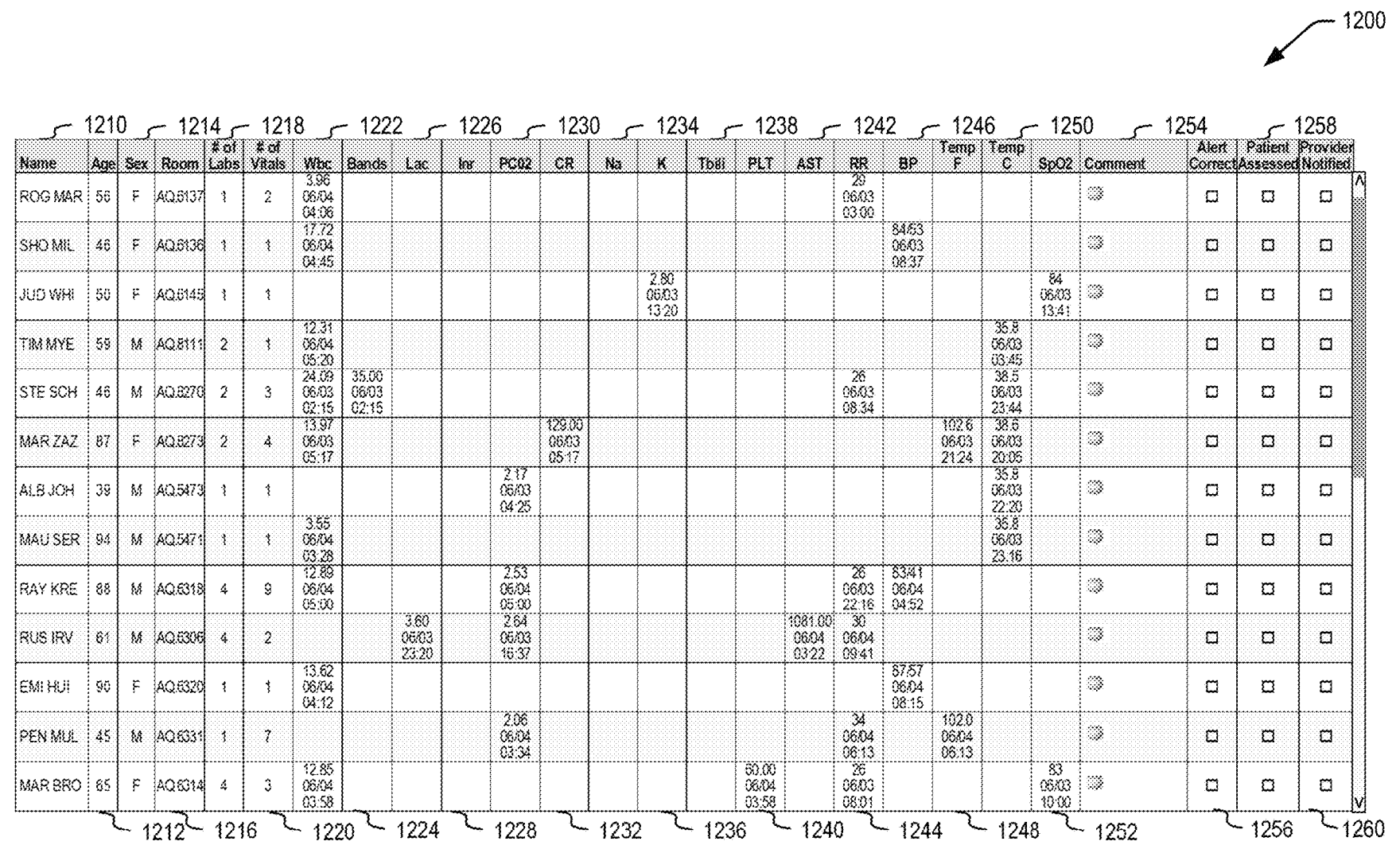

FIG. 12 shows an example of a dashboard 1200 that may be generated according to an embodiment of the invention. Dashboard 1200 may include a list of all of the dependent users for whom a flag was generated in the most recent temporal window. Dashboard 1200 may be displayed on display 920 and/or user device 930.

Dashboard 1200 may include a first column 1210 that lists an identifier of each of a plurality of dependent users. Second column 1212, third column 1214, and fourth column 1216 may list characteristics of each dependent user.

Fifth column 1218 may list the number of unique measured first parameters that have fallen within the range of values of the corresponding defined first parameter within the current temporal window. Once a measured first parameter has been noted once as falling within the range of values, it is not added again to the number in fifth column 1218 if another measurement of the same measured first parameter falls within the range of values. For example, if one of a dependent user's first parameters falls within the range of values for the corresponding defined first parameter five times within the current temporal window, fifth column 1218 only reflects the most recent result for the first parameter. Similarly, sixth column 1220 may list the number of measured second parameters that have fallen within the range of values of the corresponding defined second parameter within the current temporal window. Once a measured second parameter has been noted once as falling within the range of values, it is not added again to the number in sixth column 1220 if another measurement of the same measured second parameter falls within the range of values. For example, if one of a dependent user's second parameters falls within the range of values for the corresponding defined second parameter three times within the current temporal window, sixth column 1220 only reflects the most recent result for the second parameter.

Each of seventh column 1222, eighth column 1224, ninth column 1226, tenth column 1228, eleventh column 1230, twelfth column 1232, thirteenth column 1234, fourteenth column 1236, fifteenth column 1238, sixteenth column 1240, and seventeenth column 1242 lists the most recent measurement of a respective measured first parameter that has fallen within the range of values of the corresponding defined first parameters within the current temporal window. Each of seventh column 1222, eighth column 1224, ninth column 1226, tenth column 1228, eleventh column 1230, twelfth column 1232, thirteenth column 1234, fourteenth column 1236, fifteenth column 1238, sixteenth column 1240, and seventeenth column 1242 includes the value of the measured first parameter, the date on which the measurement was taken, and the time at which the measurement was taken. Each of seventh column 1222, eighth column 1224, ninth column 1226, tenth column 1228, eleventh column 1230, twelfth column 1232, thirteenth column 1234, fourteenth column 1236, fifteenth column 1238, sixteenth column 1240, and seventeenth column 1242 may also include any trends in the measured first parameter during the current temporal window (not shown). For example, any measurements of the measured first parameter that have fallen within the range of values of the corresponding defined measured first parameter within the current temporal window may be included.

Each of eighteenth column 1244, nineteenth column 1246, twentieth column 1248, twenty-first column 1250, and twenty-second column 1252 lists the most recent measurement of a respective measured second parameter that has fallen within the range of values of the corresponding defined respiratory rate within the current temporal window.

Each of eighteenth column 1244, nineteenth column 1246, twentieth column 1248, twenty-first column 1250, and twenty-second column 1252 includes the value of the measured second parameter, the date on which the measurement was taken, and the time at which the measurement was taken. Each of eighteenth column 1244, nineteenth column 1246, twentieth column 1248, twenty-first column 1250, and twenty-second column 1252 may also include any trends in the measured second parameter during the current temporal window (not shown). For example, any measurements of the measured second parameter that have fallen within the range of values of the corresponding defined measured second parameter within the current temporal window may be included.

Twenty-third column 1254 is a text entry field. Twenty-fourth column 1256 indicates whether an alert generated by the system was correct. For example, if at least one flag is generated for a dependent user, a basic alert is generated. A detailed alert is then sent to an authorized user, including the measured first parameters and the measured second parameters that generated the flags, along with a time frame for a response. The authorized user may indicate whether the alert was correct. For example, the alert may be incorrect if a subsequent measurement of the dependent user's first parameters and/or second parameters is outside of the range that triggered the flag.

Twenty-fifth column 1258 indicates whether a dependent user for whom a detailed was sent has been evaluated by an authorized user. Twenty-sixth column 1260 indicates whether the authorized user has been notified of the alert. Specifically, the twenty-sixth column 1260 indicates whether the detailed alert has been sent.

Figure 13:
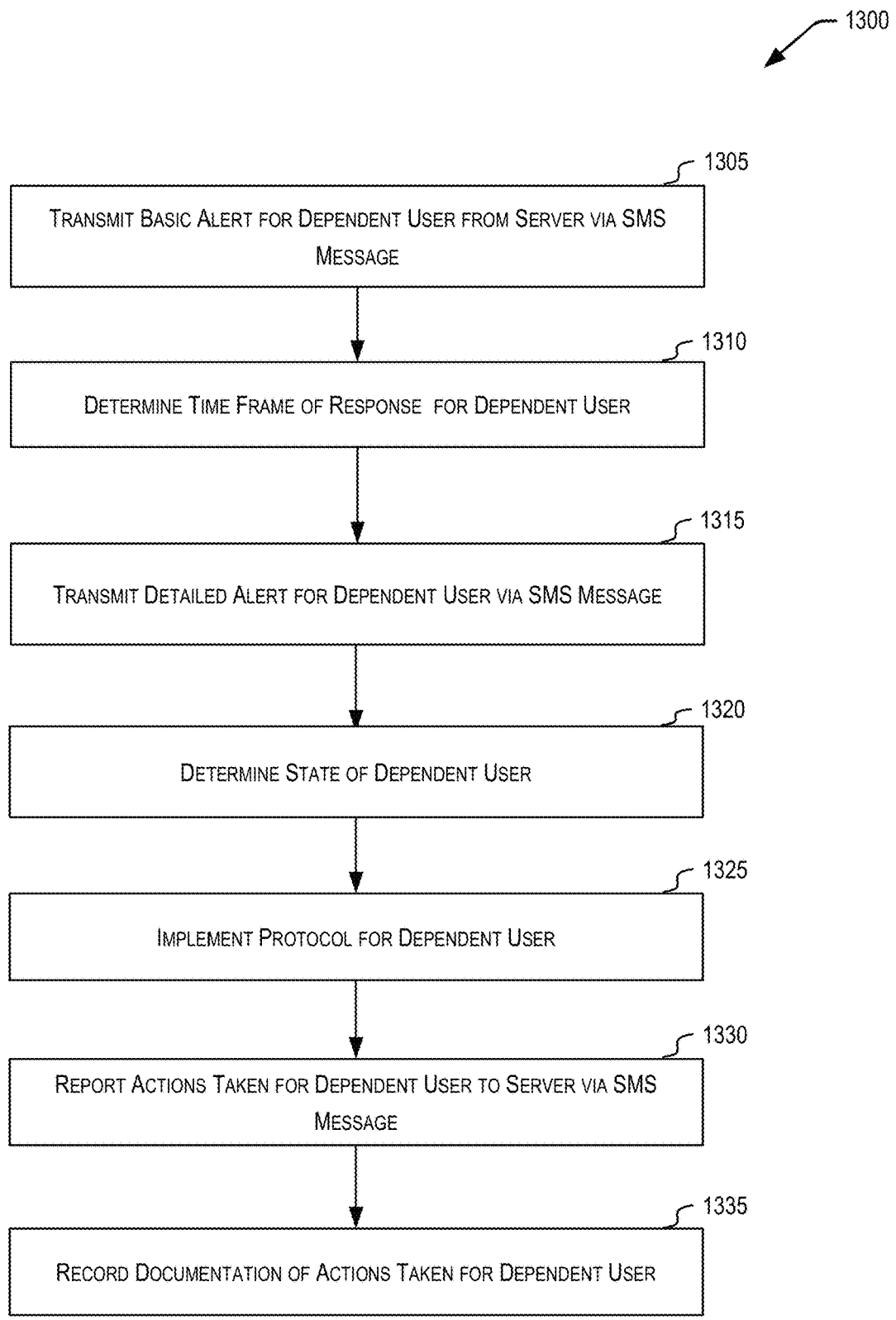
FIG. 13 is an example flowchart of a method in which techniques relating to generating a plurality of alerts relating to the state of a dependent user may be implemented, according to at least one example.

Referring now to FIG. 13, a flowchart of a method 1300 according to an example is shown. The method 1300 may generate a plurality of alerts relating to the state of a dependent user. The method 1200 may be performed by the flag generation engine 912 shown in FIG. 9.

The method 1300 begins at block 1305 where a basic alert is transmitted for a dependent user. The basic alert may include an identifier and a location of the dependent user. The basic alert may be sent by centralized server 940 to a first authorized user via SMS message. The first authorized user may receive the basic alert via user device 930.

A time frame of response for the dependent user is determined at block 1310. For example, the authorized user may view the dashboard 1200 shown in FIG. 12, and use the dashboard 1200 to determine the time frame that is needed. For example, the level of response may be a standard response to be completed within 90 minutes, a sepsis alert response to be completed within 30 minutes, or a rapid response to be completed within 15 minutes.

A detailed alert for the dependent user is sent at block 1315. The detailed alert may include an identifier of the dependent user, a location of the dependent user, the measured first parameters and the measured second parameters that generated the flags and the time frame for the response. The detailed alert may be transmitted via SMS message to a device of a second authorized user. The detailed alert may be transmitted within 17 minutes of the triggering of the flag.

The state of the dependent user is determined at block 1320. The authorized user may determine the state of the dependent user within the time frame listed in the detailed alert. Further, the second authorized user may adjust the protocol for the dependent user based on the determination.

The protocol for the dependent user may be implemented at block 1325. Any actions taken for the dependent user may be reported to centralized server 940 via SMS message at block 1330. For example, the second authorized user may use a device to transmit any changes to the protocol for the dependent user, any additional first parameters or second parameters that were obtained, and any implemented portions of the protocol for the dependent user.

The actions taken for the dependent user may be documented at block 1335. For example, the dashboard 1200 shown in FIG. 12 may be updated. A log of the first authorized user may also be updated.

FIG. 14 shows an example of a plurality of alerts 1400 that may be generated according to an embodiment of the invention. Alerts 1400 are examples of the detailed alert that may be sent at block 1315 of method 1300 shown in FIG. 13.

Figure 15:
FIG. 15 shows examples of messages that may be generated by the techniques described herein.

FIG. 15 shows an example of a plurality of messages 1500 that may be generated according to an embodiment of the invention. Messages 1500 are examples of the reports that may be sent at block 1330 of method 1300 shown in FIG. 13.

Figure 16:
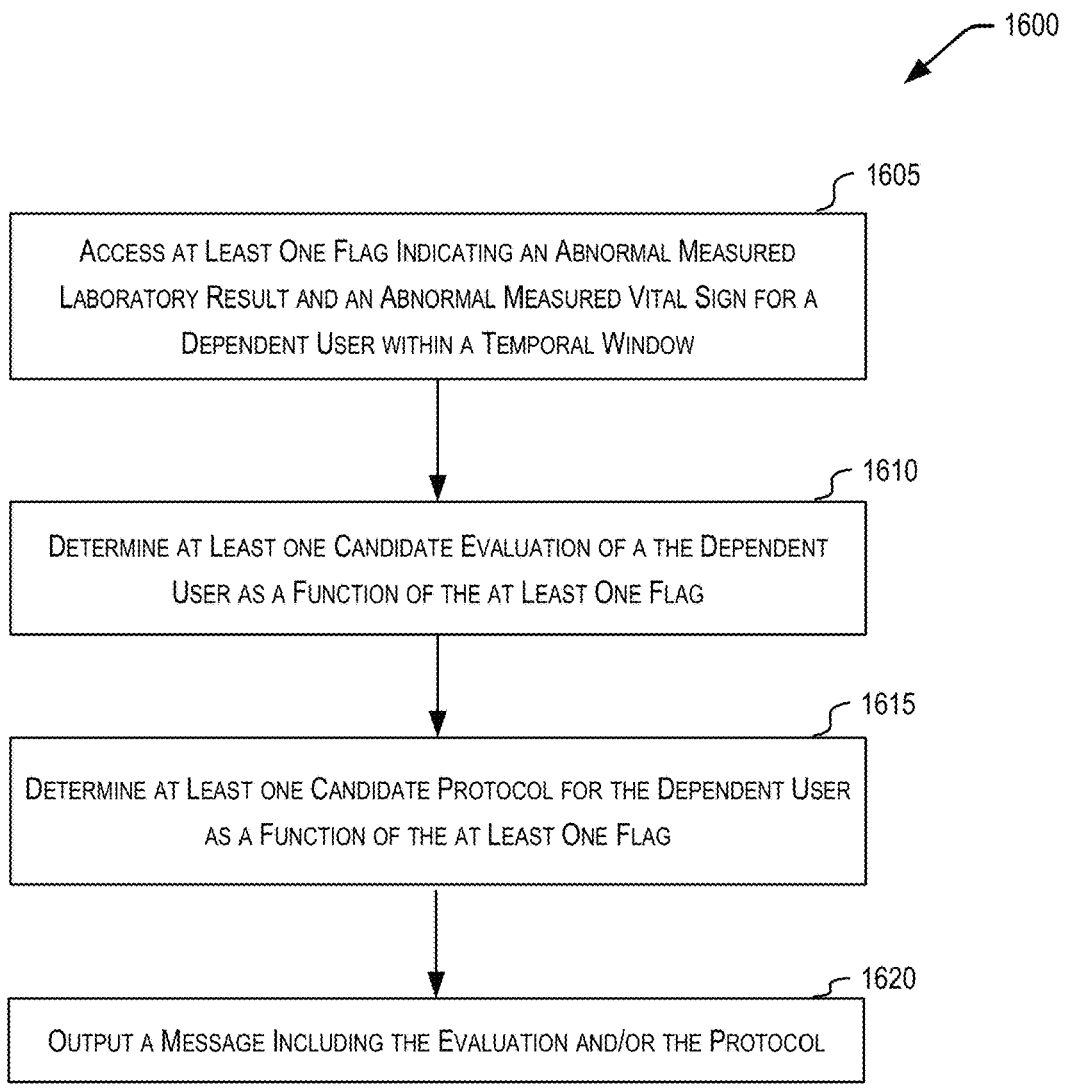
FIG. 16 is an example flowchart of a method in which techniques relating to generating a candidate evaluation and/or a candidate protocol for a dependent user may be implemented, according to at least one example.

Referring now to FIG. 16, a flowchart of a method 1600 according to an example is shown. The method 1600 may determine a candidate evaluation and/or a candidate protocol for a dependent user based on the flags that are generated for the dependent user. The method 1600 may be performed by the evaluation generation engine 913 and/or the protocol generation engine 914 shown in FIG. 9.

The method 1600 begins at block 1605 where at least one flag is accessed for a dependent user. Each flag may be generated by method 1000 shown in FIG. 10. Each flag may be accessed from general data store 918 shown in FIG. 9. Each flag includes a measured first parameter that is within the range of values for the respective defined first parameter and a measured second parameter that is within the range of values for the respective defined second parameter. The measured first parameter and the measured second parameter are measured within the same temporal window.

At least one candidate evaluation of a state of the dependent user may be determined at block 1610. The candidate evaluation may be determined by inputting the dependent user's flags as parameters into an artificial intelligence engine, which may compare the dependent user's flags against a database of historical dependent user data that includes evaluations made for various combinations of the measured first parameters and the measured second parameters within the flags. At least one candidate protocol for the dependent user may be determined at block 1615.

Alternatively, it may not be necessary to determine a single evaluation of the dependent user's state. Instead, the dependent user's flags may be analyzed to generate a set of differential evaluations for the dependent user. For example, three candidate evaluations may be generated and ranked according to likelihood, based on the components of the flags for the dependent user. The candidate protocol may be determined based on the differential evaluations.

A message including the candidate evaluation and/or the candidate protocol for the dependent user may be output at block 1620 to display 920, user device 930, and/or centralized server 940. Alternatively or in addition, the message may be stored in general data store 918.

Figure 17:
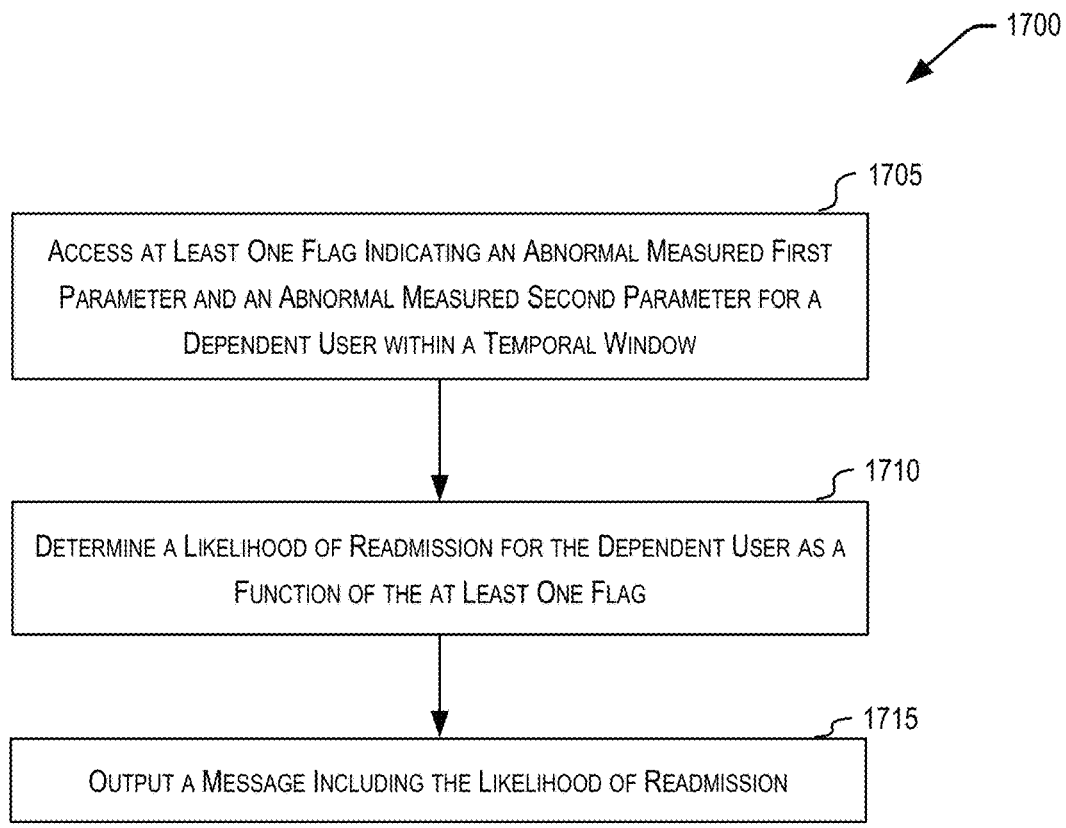
FIG. 17 is an example flowchart of a method in which techniques relating to determining a likelihood of readmission for a dependent user may be implemented, according to at least one example.

Referring now to FIG. 17, a flowchart of a method 1700 according to an example is shown. The method 1700 may determine a likelihood of readmission for a dependent user based on the flags that are generated for the dependent user. The method 1700 may be performed by the readmission analysis engine 915 shown in FIG. 9.

The method 1700 begins at block 1705 where at least one flag is accessed for a dependent user. Each flag may be generated by method 1000 shown in FIG. 10. Each flag may be accessed from general data store 918 shown in FIG. 9.

Each flag includes a measured first parameter that is within the range of values for the respective defined first parameter and a measured second parameter that is within the range of values for the respective defined second parameter. The measured first parameter and the measured second parameter are measured within the same temporal window.

A likelihood of readmission for the dependent user may be determined at block 1710. The likelihood of readmission may be determined by inputting the dependent user's flags as parameters into an artificial intelligence engine, which may compare the dependent user's flags against a database of historical dependent user data that includes readmission rates for various combinations of the measured first parameters and the measured second parameters within the flags.

A message including the likelihood of readmission for the dependent user may be output at block 1715 to display 920, user device 930, and/or centralized server 940. Alternatively or in addition, the message may be stored in general data store 918.

Figure 18:
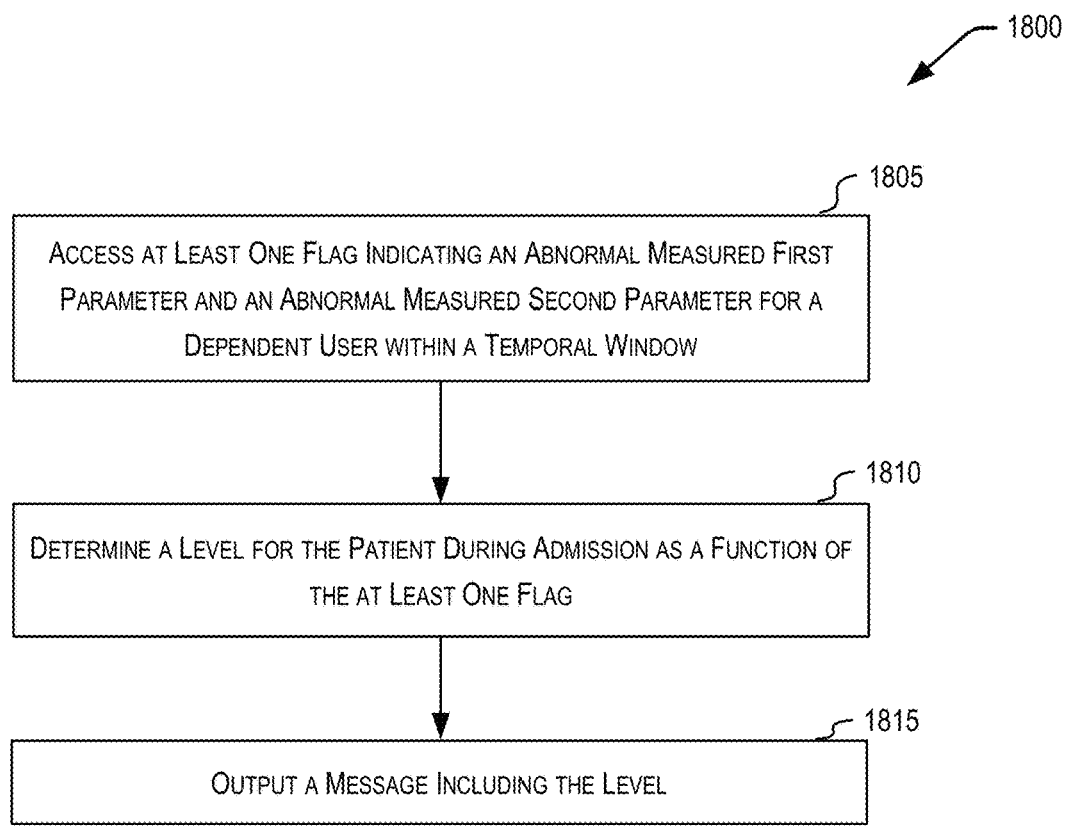
FIG. 18 is an example flowchart of a method in which techniques relating to determining a level for a dependent user may be implemented, according to at least one example.

Referring now to FIG. 18, a flowchart of a method 1800 according to an example is shown. The method 1800 may determine a level for a dependent user based on the flags that are generated for the dependent user. The method 1800 may be performed by the admission analysis engine 916 shown in FIG. 9.

The method 1800 begins at block 1805 where at least one flag is accessed for a dependent user. Each flag may be generated by method 1000 shown in FIG. 10. Each flag may be accessed from general data store 918 shown in FIG. 9. Each flag includes a measured first parameter that is within the range of values for the respective defined first parameter and a measured second parameter that is within the range of values for the respective defined second parameter. The measured first parameter and the measured second parameter are measured within the same temporal window.

A level for the dependent user may be determined at block 1810. For example, a suitable number of first parameters and second parameters may be obtained for the dependent user. The flags generated may be used to determine the level of the dependent user. The level may be determined by inputting the dependent user's flags as parameters into an artificial intelligence engine, which may compare the dependent user's flags against a database of historical dependent user data that includes the level for various combinations of the measured first parameters and the measured second parameters within the flags.

A message including the level for the dependent user may be output at block 1815 to display 920, user device 930, and/or centralized server 940. Alternatively or in addition, the message may be stored in general data store 918.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method of determining a state of a dependent user, the computer-implemented method comprising:
storing rules in a non-transitory, machine-readable storage medium, where the rules comprise machine-learned rules;
using the machine-learned rules to execute one or more data query scripts to query one or more data stores, and, consequent to execution of the one or more data query scripts in accordance with the machine-learned rules, receiving data for the dependent user from a data warehouse, wherein:
the data comprises a plurality of measured laboratory results and a plurality of measured vital signs,
the data is provided to the data warehouse from a plurality of data sources, and
at least some of the data is converted according to conversion rules of the rules to a second format from a first format in which the at least some of the data is provided by at least one data source of the plurality of data sources;
accessing a rule set of the rules for the dependent user, wherein the rule set comprises a range of values for each of a plurality of defined laboratory results and a range of values for each of a plurality of defined vital signs, and the rule set is a function of a location of the dependent user;
for a subset of the data that is collected within a temporal window:
for at least one measured laboratory result of the plurality of measured laboratory results, comparing the measured laboratory result with a respective one of the plurality of the defined laboratory results to determine whether the measured laboratory result is within the range of values for the respective one of the plurality of defined laboratory results;
for at least one measured vital sign of the plurality of measured vital signs, comparing the measured vital sign with a respective one of the plurality of the defined vital signs to determine whether the measured vital sign is within the range of values for the respective one of the plurality of defined vital signs; and
if it is determined that at least one of the measured laboratory results is within the range of values for the respective one of the plurality of the defined laboratory results and it is determined that at least one of the measured vital signs is within the range of values for the respective one of the plurality of the defined vital signs:
generating a flag indicating that the state of the dependent user is deteriorating;
outputting a message comprising an identifier of the dependent user, the flag, the at least one of the measured laboratory results that is within the range of values for the respective one of the plurality of the defined laboratory results, and the at least one of the measured vital signs is within the range of values for the respective one of the plurality of the defined vital signs;
determining at least one candidate diagnosis of a condition of the dependent user as a function of the flag;
determining at least one candidate treatment of the dependent user as a function of the at least one candidate diagnosis; and
treating the dependent user according to the at least one candidate treatment.

2. The computer-implemented method of claim 1, further comprising processing the data to filter out invalid entries.

3. The computer-implemented method of claim 1, wherein the rule set is a function of a classification of the dependent user.

4. The computer-implemented method of claim 1, wherein the message further comprises a level of response for the state of the dependent user.

5. The computer-implemented method of claim 4, wherein the message further comprises a time frame for the response.

6. A system of determining a state of a dependent user, the system comprising:
one or more data processors; and
a non-transitory, computer-readable storage medium containing instructions that, when executed on the one or more data processors, cause the one or more data processors to perform actions including:
storing rules comprising machine-learned rules;
using the machine-learned rules to execute one or more data query scripts to query one or more data stores, and, consequent to execution of the one or more data query scripts in accordance with the machine-learned rules, receiving data for the dependent user from a data warehouse, wherein:
the data comprises a plurality of measured laboratory results and a plurality of measured vital signs,
the data is provided to the data warehouse from a plurality of data sources, and
at least some of the data is converted according to conversion rules of the rules to a second format from a first format in which the at least some of the data is provided by at least one data source of the plurality of data sources;
accessing a rule set of the rules for the dependent user, wherein the rule set comprises a range of values for each of a plurality of defined laboratory results and a range of values for each of a plurality of defined vital signs, and the rule set is a function of a location of the dependent user;
for a subset of the data that is collected within a temporal window:
for at least one measured laboratory result of the plurality of measured laboratory results, comparing the measured laboratory result with a respective one of the plurality of the defined laboratory results to determine whether the measured laboratory result is within the range of values for the respective one of the plurality of defined laboratory results;
for at least one measured vital sign of the plurality of measured vital signs, comparing the measured vital sign with a respective one of the plurality of the defined vital signs to determine whether the measured vital sign is within the range of values for the respective one of the plurality of defined vital signs; and
if it is determined that at least one of the measured laboratory results is within the range of values for the respective one of the plurality of the defined laboratory results and it is determined that at least one of the measured vital signs is within the range of values for the respective one of the plurality of the defined vital signs:

generating a flag indicating that the state of the dependent user is deteriorating;

outputting a message comprising an identifier of the dependent user, the flag, the at least one of the measured laboratory results that is within the range of values for the respective one of the plurality of the defined laboratory results, and the at least one of the measured vital signs is within the range of values for the respective one of the plurality of the defined vital signs;

determining at least one candidate diagnosis of a condition of the dependent user as a function of the flag;

determining at least one candidate treatment of the dependent user as a function of the at least one candidate diagnosis; and treating the dependent user according to the at least one candidate treatment.

7. The system of claim 6, wherein the actions further include processing the data to filter out invalid entries.

8. The system of claim 6, wherein the rule set is a function of a classification of the dependent user.

9. The system of claim 6, wherein the message further comprises a level of response for the state of the dependent user.

10. The system of claim 9, wherein the message further comprises a time frame for the response.

11. A computer-program product tangibly embodied in a non-transitory, machine-readable storage medium, including instructions configured to cause one or more data processors to perform actions for determining a state of a dependent user, the actions including:

storing rules comprising machine-learned rules;

using the machine-learned rules to execute one or more data query scripts to query one or more data stores, and, consequent to execution of the one or more data query scripts in accordance with the machine-learned rules, receiving data for the dependent user from a data warehouse, wherein:

the data comprises a plurality of measured laboratory results and a plurality of measured vital signs, the data is provided to the data warehouse from a plurality of data sources, and at least some of the data is converted according to conversion rules of the rules to a second format from a first format in which the at least some of the data is provided by at least one data source of the plurality of data sources;

accessing a rule set of the rules for the dependent user, wherein the rule set comprises a range of values for each of a plurality of defined laboratory results and a range of values for each of a plurality of defined vital signs, and the rule set is a function of a location of the dependent user;

for a subset of the data that is collected within a temporal window:

for at least one measured laboratory result of the plurality of measured laboratory results, comparing the measured laboratory result with a respective one of the plurality of the defined laboratory results to determine whether the measured laboratory result is within the range of values for the respective one of the plurality of defined laboratory results;

for at least one measured vital sign of the plurality of measured vital signs, comparing the measured vital sign with a respective one of the plurality of the defined vital signs to determine whether the measured vital sign is within the range of values for the respective one of the plurality of defined vital signs; and if it is determined that at least one of the measured laboratory results is within the range of values for the respective one of the plurality of the defined laboratory results and it is determined that at least one of the measured vital signs is within the range of values for the respective one of the plurality of the defined vital signs:

generating a flag indicating that the state of the dependent user is deteriorating;

outputting a message comprising an identifier of the dependent user, the flag, the at least one of the measured laboratory results that is within the range of values for the respective one of the plurality of the defined laboratory results, and the at least one of the measured vital signs is within the range of values for the respective one of the plurality of the defined vital signs;

determining at least one candidate diagnosis of a condition of the dependent user as a function of the flag;

determining at least one candidate treatment of the dependent user as a function of the at least one candidate diagnosis; and treating the dependent user according to the at least one candidate treatment.

12. The computer-program product of claim 11, wherein the actions further include processing the data to filter out invalid entries.

13. The computer-program product of claim 11, wherein the rule set is a function of a classification of the dependent user.

14. The computer-program product of claim 11, wherein the message further comprises a level of response for the state of the dependent user.

15. The computer-program product of claim 14, wherein the message further comprises a time frame for the response.

\* \* \* \* \*